(12) United States Patent
Thompson et al.

(10) Patent No.: US 9,193,990 B2
(45) Date of Patent: Nov. 24, 2015

(54) BIOLUMINESCENT METAL ION ASSAY

(71) Applicant: Richard B. Thompson, Baltimore, MD (US)

(72) Inventors: Richard B. Thompson, Baltimore, MD (US); Evgenia Matveeva, Rockville, MD (US); Carol Fierke, Ann Arbor, MI (US); Leslie Bourne, Coatesville, PA (US); Graham Franke, Baltimore, MD (US)

(73) Assignee: Richard B. Thompson, Baltimore, MD (US)

( * ) Notice: Subject to any disclaimer, the term of this patent is extended or adjusted under 35 U.S.C. 154(b) by 0 days.

(21) Appl. No.: 14/218,085

(22) Filed: Mar. 18, 2014

(65) Prior Publication Data

US 2014/0273038 A1 Sep. 18, 2014

Related U.S. Application Data

(60) Provisional application No. 61/799,348, filed on Mar. 15, 2013.

(51) Int. Cl.
*C12Q 1/66* (2006.01)
*G01N 33/542* (2006.01)

(52) U.S. Cl.
CPC .............. *C12Q 1/66* (2013.01); *G01N 33/542* (2013.01); *G01N 2333/988* (2013.01)

(58) Field of Classification Search
IPC ........................................................ C12Q 1/66
See application file for complete search history.

(56) References Cited

U.S. PATENT DOCUMENTS

| 6,197,258 | B1* | 3/2001 | Thompson et al. | 422/82.07 |
| 2002/0055091 | A1* | 5/2002 | Thompson et al. | 435/4 |
| 2005/0250170 | A1* | 11/2005 | Thompson et al. | 435/18 |
| 2008/0138291 | A1 | 6/2008 | Supuran et al. | |
| 2009/0042311 | A1* | 2/2009 | Thompson | 436/164 |

OTHER PUBLICATIONS

Thompson R. et al. Fibert Optic Biosensor for Co and Cu Based of Fluorescence Energy Transfer With an Enzyme Transducer. Biosensors & Bioelectronics 11(6/7)557-564, 1996.*
Thompson R. et al. Determination of Multiple Analytes Using a Fiber Optic Biosensor Based on Fluorescence Energy Transfer. SPIE 2680 47-56.*
Rami et al. "Synthesis of rhodamine B—benzenesulfonamide conjugates and their inhibitory activity against human α-and bacterial/fungal β-carbonic anhydrases", Bioorganic & Medicinal Chemistry Letters 21 (2011) 5210-5213.

* cited by examiner

*Primary Examiner* — Ralph Gitomer
(74) *Attorney, Agent, or Firm* — Roberts Mlotkowski Safran & Cole, P.C.

(57) ABSTRACT

A method for determining metal ions, both qualitatively and quantitatively, is disclosed. The method utilizes emission from fluorescence resonance energy transfer from a luciferase-carbonic anhydrase conjugate or fusion protein to an acceptor ligand in the presence of metal ion bound to the protein to measure free metal ion concentrations down to picomolar concentration ranges. The method is relatively insensitive to contaminants, and so can be used to measure metal ion concentrations in cells, body fluids or environmental samples without extensive sample preparation.

26 Claims, 4 Drawing Sheets

BIOLUMINESCENT METAL ION ASSAY

RELATED APPLICATIONS

This application claims benefit of provisional application 61/799,348, filed Mar. 15, 2013.

FIELD OF THE INVENTION

The field of the invention generally relates to methods of determining metal ions in aqueous samples.

DESCRIPTION OF THE INVENTION

Figure 1:
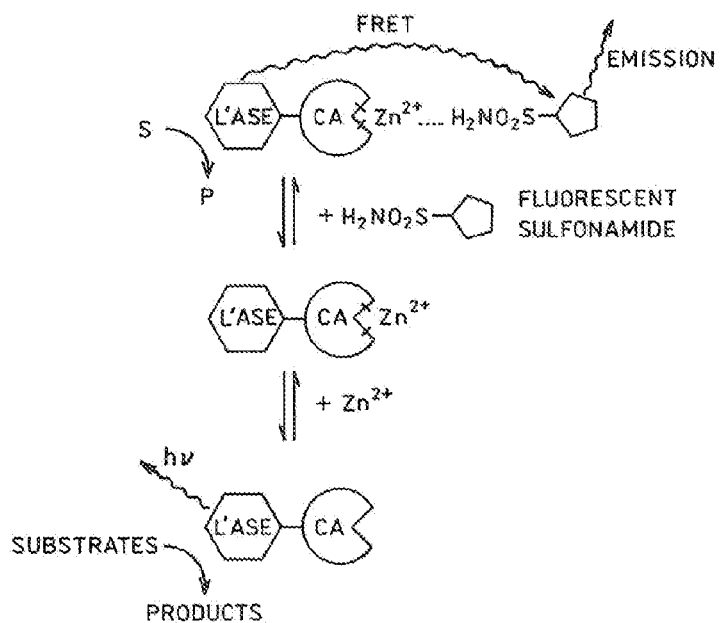
FIG. 1 illustrates the principle of the bioluminescence FRET assay

Articles of the patent and periodical literature are cited throughout this document. Each cited article is hereby incorporated by reference in its entirety and for all purposes by such citation.

Determination of metal ions in aqueous samples is frequently useful and important, for many reasons. For instance, some metal ions such as copper, zinc, cadmium, and nickel are important nutrients or pollutants in natural waters such as sea water, fresh water, lakes, streams, and the like. In biomedical sciences, determining metal ions is important for determining the health of a patient, his/her nutritional state, or the presence of disease. Frequently, these metal ions must be determined at low levels, so methods must be sensitive and selective for the metal ion of interest, particularly when similar metal ions are known or likely to be present. For some applications, the determination must be quantitative. In some cases the metal content of a sample can be determined by first processing the sample to a form more amenable to the analytical method. In many aqueous samples, the metal ion is bound to one or more ligands. In some cases these ligands rapidly adsorb to and desorb from the metal ion, permitting other ligands to take their places (the metal ion is sometimes termed "free" in these cases); in other cases adsorption and desorption may be much slower and in some cases the adsorption is slow enough to be essentially irreversible (Stumm and Morgan 1996). In some cases the determination of metal content is made difficult because it is preferable to determine the metal in situ, and in vivo, inside the human body.

Many methods are known to the art for determining metal ions in samples, particularly aqueous samples. These include electrochemical methods such as ion-selective electrodes or anodic stripping voltammetry, ion chromatography, atomic absorption or emission spectroscopy, inductively-coupled plasma mass spectroscopy (ICP-MS), absorbance or fluorescence spectroscopy using an added indicator, and bioassays. Most of these methods are accurate, sensitive, and selective for many analytes in different types of samples. Nearly all these methods require that a sample be acquired and submitted to the method, typically by bringing the sample to an instrument. Moreover, nearly all require a sophisticated and costly instrument for the determination, together with a skilled person to operate the instrument and perhaps prepare the sample, together with a suitable laboratory space with electricity and air conditioning. These shortcomings (among others) of the prior art make it difficult or altogether infeasible to make such determinations in living organisms, because most of these methods require removal of a sample from the organism or person prior to the analysis, which may be uncomfortable, unethical, or actually hazardous for the person or organism. Similarly, these issues make it difficult to perform such determinations in the field or under austere conditions, such as might be found in a tribal village or anywhere following a natural disaster or war, where laboratory space with electricity or air conditioning might not exist. Thus the present invention is particularly suited for field or home measurements, and measurements in living organisms.

We have developed several fluorescence-based assays for metal ions which mainly employ variants of the enzyme carbonic anhydrase to recognize and bind the metal ion analyte, and transduce its presence or level as changes in fluorescence intensity, lifetime, spectra, and/or anisotropy (polarization). These assays are sensitive, selective, accurate, reproducible, and robust enough that they have been used to determine metal ions in matrices as complex as sea water, ground water, serum, growth media, or cytoplasm (Thompson and Patchan 1995; Elbaum, Nair et al. 1996; Thompson, Maliwal et al. 1998; Thompson, Zeng et al. 2000; Thompson, Cramer et al. 2002; Zeng, Thompson et al. 2003; Bozym, Hurst et al. 2008). They also have been incorporated into fiber optics, such that metal ions may be determined in living organisms or remote and inaccessible places (reviewed in (Thompson 1991; Thompson 1994; Thompson, Hui-Hui Zeng et al. 2008)). A drawback of the fiber optic sensors is they only determine the metal ion at a single point (the distal tip of the fiber) instead of throughout the organism.

Some of the prior art fluorescence assays developed by ourselves and others utilize a phenomenon called Förster resonance energy transfer, abbreviated as FRET. The physical basis of FRET is described in detail by Forster (Forster 1948) and basically is that an atom or molecule in an excited state (called the donor) can transfer its energy through a dipole-dipole mechanism to a second molecule or atom (termed the acceptor] if (in addition to other factors) 1) the donor and acceptor are close enough together in space, 2) their transition dipoles are close to parallel, and 3) there is significant overlap between the characteristic emission wavelengths of the donor's emission and the acceptor's absorbance, all during the time the donor is in the excited state. If the acceptor is also fluorescent it can emit at its characteristic emission wavelengths following the energy transfer. Note that the efficiency of the process depends strongly on the above-listed criteria and can be predicted knowing their values using Forster's theory. Also note that if these conditions are met the acceptor described above can also serve as donor to a third molecule or atom (an "ultimate acceptor") which then would subsequently emit at the ultimate acceptor's characteristic emission wavelengths. For instance, a FRET-based zinc assay is known which transduces the metal ion level as a ratio of fluorescence intensities measured at the acceptor's emission wavelengths using two different excitation wavelengths (Thompson, Cramer et al. 2002). Also known is determination of copper ion by FRET from a fluorescent label conjugated to apocarbonic anhydrase acting as donor to the weak d-d absorbance of the copper ion bound to the carbonic anhydrase; the level of copper ion is preferably measured by the change in fluorescence lifetime of the label (Thompson, Ge et al. 1996). In both these examples a fluorometer operated by a trained person is necessary to perform these measurements.

Another form of luminescence well known to the art is called bioluminescence, wherein a catalyst (typically an enzyme) acts on a substrate (usually termed generically a luciferin) to perform a chemical reaction which results in an electronic excited state that emits light. Thus the commonly observed yellow-green emission from the abdomen of a firefly (*Photinus pyralis*) results from firefly luciferase oxidizing a compound called luciferin with concomitant hydrolysis of ATP (adenosine trisphosphate) and emission of light. The phenomenon of bioluminescence is well known to the art, but the molecular details of how the light is produced are still under active investigation.

Investigators have utilized bioluminescence in chemical assays. For instance, firefly luciferase and luciferin have for decades been used to measure ATP and processes that produce ATP, such as oxidative phosphorylation. More recently, the Packard Biosciences corporation and others developed assays (P. Dionne, et al., "BRET2: Efficient energy transfer from *Renilla* luciferase to GFP to measure protein-protein interaction and intracellular signaling events in live cells," in *Luminescence Biotechnology Instruments and Applications*, Chap 42, CRC Press, Boca Raton, Fla.) and immunoassays (R. Arai, et al., "Demonstration of a homogenous noncompetitive immunoassay based on bioluminescence resonance energy transfer," *Analytical Biochemistry* 289, 77-81 (2001)) that use bioluminescence resonance energy transfer. In a typical immunoassay, a first antibody is labeled with luciferase and combined in dilute solution together with a sample containing an antigen having two epitopes: one recognized by the first antibody and a second epitope recognized by a second antibody labeled with a fluorescent acceptor such as EYFP, also present in the mix. If the antigen is present in the sample and the luciferase substrate(s) are added to the mix, the acceptor is brought into close proximity to the luciferase by the binding of the antibodies to which they are attached binding to their respective epitopes on the antigen, and some light emission is observed at the characteristic wavelengths of the acceptor. A key advantage of such bioluminescent assays is the low amount of background luminescence compared with fluorescence (and consequent high sensitivity), since fluorescent impurities if present do not get excited by the luciferase-catalyzed reaction. However, immunoassays are poorly suited to determination of metal ions, because it is difficult to raise antibodies that recognize particular free metal ions: injection of a rabbit or goat with zinc ion or Cu(II) might be toxic to the animal, but would not elicit production of antibodies that recognized the metal ion. Moreover, the metal ion does not possess the two different epitopes recognized by two separate antibodies taught by Arai, et al.; thus combination of (Thompson, Cramer et al. 2002) or (Thompson, Ge et al. 1996) with Arai, et al., is not workable.

Other investigators (M. DeLuca and W. D. McElroy, "Purification and properties of firefly luciferase," in *Methods in Enzymology Vol. 57 Chemiluminescence and Bioluminescence* (M. A. DeLuca, ed.) pp.3-15 (1978)) discovered that the presence of relatively high concentrations of certain metal ions produced modest changes in the characteristic peak emission wavelengths of certain luciferases, and proposed that these phenomena could be used to determine metal ions such as Zn(II) and Pb(II). However, the changes are modest and require high concentrations of the metals, making them neither selective nor sensitive enough for determinations of these metals at trace levels in complex matrices as we have accomplished.

Figure 2:
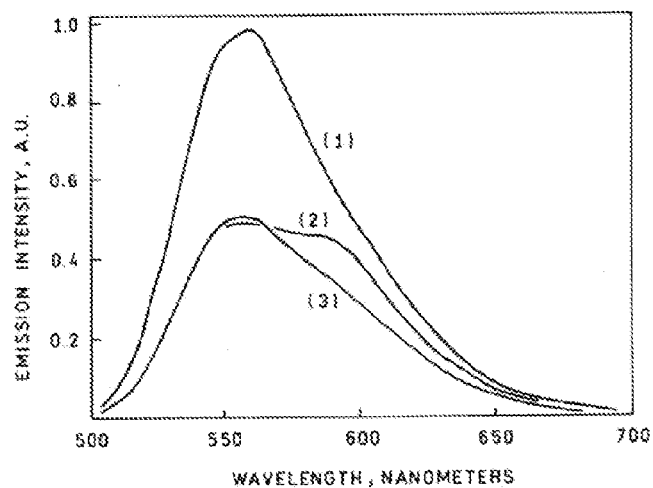
FIG. 2 shows bioluminescence emission spectra from 1) firefly luciferase-holoCA fusion protein in the absence of UAL; 2) following addition of LISSAMINE rhodamine sulfonamide (the UAL), and 3) following addition of acetazolamide (Diamox).

The principle of the present invention is illustrated in FIG. 1. The luciferase enzyme is conjugated to the carbonic anhydrase either by chemical means well known to the art using crosslinking reagents (*Pierce Catalog and Handbook*, Pierce Chemical Company, Rockford, Ill. (1994) pp. 155-201) or avidin-biotin chemistry (D. Savage, et al., *Avidin-Biotin Chemistry: A Handbook*, Pierce Chemical Co., Rockford, Ill., (1992)), or the gene for the luciferase enzyme subunit(s) is fused through a short linker to the gene for the carbonic anhydrase and the fused gene expressed to produce a fusion protein. As a non-limiting example, consider that if free zinc ion is present in the solution at concentrations at or above its $K_D$ for binding to carbonic anhydrase ($K_D$~4 picomolar for wild type human carbonic anhydrase II) with the luciferase-carbonic anhydrase conjugate, it will bind to the apocarbonic anhydrase to form holocarbonic anhydrase; if the ultimate acceptor ligand ("UAL", such as the reaction product of LISSAMINE rhodamine sulfonyl chloride with p-(2-aminoethyl) benzene sulfonamide, Scheme 1, which we call LISSAMINE rhodamine sulfonamide for short) is present in the solution, it will bind to the holocarbonic anhydrase. Note that the ultimate acceptor ligand is not the same as ligands discussed elsewhere in the specification as binding to metal ions in solution; it may bind poorly to some metal ions ($K_D$>millimolar) but functionally it is desirable that the UAL bind tightly to holocarbonic anhydrase ($K_D$≤micromolar) but poorly to the apocarbonic anhydrase or free metal ion(s). The UAL in this case is chosen to have a good spectral overlap between the bioluminescence of the luciferase in use and the absorbance spectrum of the ultimate acceptor ligand. In the case of LISSAMINE rhodamine sulfonamide the overlap of its absorbance ($\lambda$max=588 nm) with the characteristic emission wavelengths of *Photinus pyralis* firefly luciferase ($\lambda$max=570 nm) is excellent, so energy transfer between the two is relatively efficient. Thus, if zinc is not present in the CA binding site the ultimate acceptor ligand does not bind, it is not (on average) close to the luciferase and no energy transfer occurs, such that the native bioluminescence of the luciferase is observed in the yellow portion of the spectrum with a peaki at 570 nm when ATP and luciferin (the luciferase substrates) are added (FIG. 2). If zinc is present at high enough concentration, the ultimate acceptor ligand (LISSAMINE rhodamine sulfonamide) binds to the holocarbonic anhydrase and is now close enough to act as a FRET energy acceptor from the luciferase, such that when the luciferase substrate(s) are added the excited state energy is transferred to the ultimate acceptor ligand which in turn emits at its characteristic wavelengths peaking in the orange at 590 nm. If a competing sulfonamide with much higher affinity for holoCA is added such as acetazolamide (Diamox), it competes for the sulfonamide binding site with the LISSAMINE rhodamine sulfonamide which is thus displaced, and the unperturbed bioluminescence emission spectrum of the luciferase is restored (FIG. 2). This control experiment demonstrates that the binding of the LISSAMINE rhodamine sulfonamide is to the active site and is specific (since it can be completely displaced by the acetazolamide), and not some form of non-specific binding to the carbonic anhydrase. The free zinc concentration can be related to the amount of orange emission, or preferably to the levels of luciferase emission and ultimate acceptor emission, or their ratio, which is proportional to zinc concentration.

In a preferred embodiment the luciferase is from firefly, the substrates are luciferin (D-(+2-(6'-hydroxy-2'benzothiazolyl)-$\Delta^2$-thiazoline-4-carboxylic acid) and adenosine trisphosphate (ATP), the carbonic anhydrase variant is human H36C-apocarbonic anhydrase II, the ultimate acceptor ligand is LISSAMINE rhodamine sulfonamide, and the luciferase and carbonic anhydrase are conjugated by the heterobifunctional crosslinker Sulfo-SMCC. Other luciferases (such as those from bacterial and dinoflagellate species and variants thereof), luciferase substrates suited for the particular luciferase, carbonic anhydrase variants, means of connecting the luciferase and carbonic anhydrase, and/or ultimate acceptor ligands (such as fluorescent sulfonamides disclosed in (Elbaum, Nair et al. 1996; Thompson, Jr. et al. 2000; Thompson, Maliwal et al. 2000)) may be substituted in the invention by means well known to the art provided that the energy transfer from the luciferase to the ultimate acceptor ligand is reasonably efficient when the ultimate acceptor ligand is bound to the protein, and poor or absent when it is not. Efficiency of energy transfer can be predicted from the emission spectrum of the luciferase bioluminescence, the absorbance spectrum of the UAL, the refractive index of the medium between the donor and acceptor, an estimated relative orientation of the donor and acceptor, and the quantum yield of the donor by the well-known theory of Forster (Forster 1948). The "characteristic wavelengths" of the bioluminescent emission, intervening acceptor absorbance and emission, and ultimate acceptor ligand absorbance and emission refer to the typical bioluminescent emission spectra, absorbance spectra, and emission spectra or parts thereof for those respective species, which typically change only slightly under various environmental conditions of solvent, temperature, and pressure. Thus, fluorescein sulfonamide typically exhibits a peak absorbance at 495 nm and an emission peak at 510 nm, but those exact wavelengths and the detailed shape of the spectra may vary slightly with conditions, and not affect the functioning of the invention to an important extent. Thus small changes in the spectra may affect the efficiency of energy transfer and the exact values of the ratios to a minor extent, without affecting the overall functioning of the invention; it is best to perform calibrations under conditions as similar as possible to those used for measuring the sample of interest.

In some embodiments it may be desirable to measure the free metal ion inside a living cell or multicellular living organism; under those conditions it is desirable to introduce the luciferase-carbonic anhydrase conjugate into the cell either by expressing a fusion protein by transfecting the fused genes of the luciferase and CA as previously described for other genes fused with that of carbonic anhydrase (Wang, Hurst et al. 2011; McCranor, Bozym et al. 2012), or by putting a TAT-tag on the fused protein (Schwarze, Ho et al. 1999; Bozym, Thompson et al. 2006), or by microinjecting the protein. Genes for luciferase and carbonic anhydrase variants may be fused by means well known to the art and used to transfect prokaryotic (Wang, Hurst et al. 2011) or eukaryotic cells (McCranor, Bozym et al. 2012). For example, DNA of the fused luciferase and CA genes may be transferred into cells by use of a reagent such as LIPOFECTAMINE.

Figure 3:
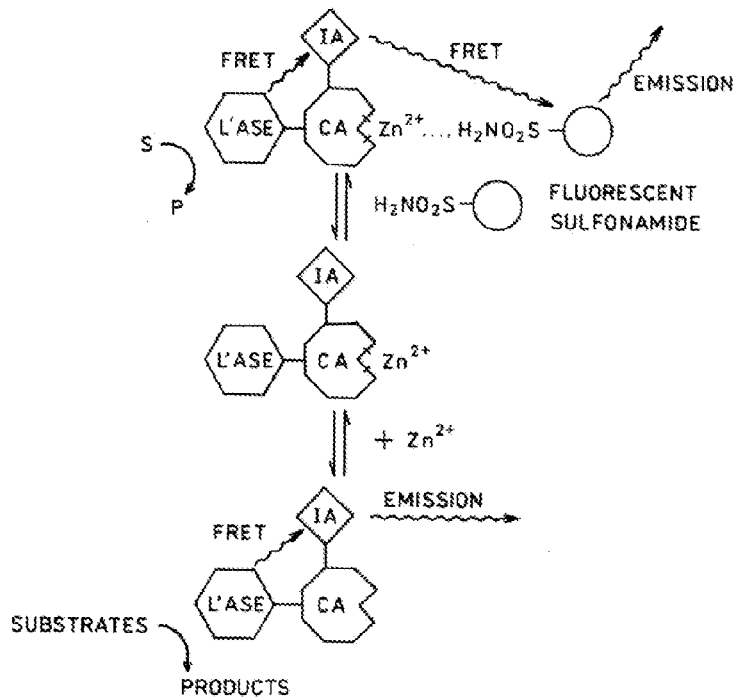
FIG. 3 illustrates the principle of a sensor utilizing an intervening acceptor (IA).

In some embodiments where the metal ion is to be measured in a highly scattering medium such as turbid solution or living tissue, or a visibly colored solution, it may be desirable for the UAL emission to be in the red or near infrared portions of the electromagnetic spectrum to minimize these interfering effects. Furthermore, a UAL that absorbs well at the characteristic emission wavelengths of the luciferase and also emits at sufficiently long wavelengths (perhaps 800 nm) may not be available. In these instances, one may conjugate an additional fluorescent molecule to the luciferase-carbonic anhydrase conjugate to serve as an intervening acceptor (IA, FIG. 3). The spectroscopic properties of the intervening acceptor are such that it has a good overlap of its absorbance spectrum with the luciferase emission, and a good overlap of its emission wavelengths with the ultimate acceptor absorbance spectrum. The intervening acceptor may be a small fluorophore conjugated to the protein by means well known to the art, or a fluorescent protein expressed from a gene fused with the luciferase and/or carbonic anhydrase genes. In a preferred embodiment the intervening acceptor is naphthofluorescein carboxylic acid N-hydroxysuccinimidyl ester (Molecular Probes/Invitrogen C-653) conjugated to CA and the ultimate acceptor ligand is the product of reaction of IR-800 dye succinimidyl ester (LiCor, Lincoln, Me.) with p-(2-aminoethane)benzenesulfonamide.

Figure 4:
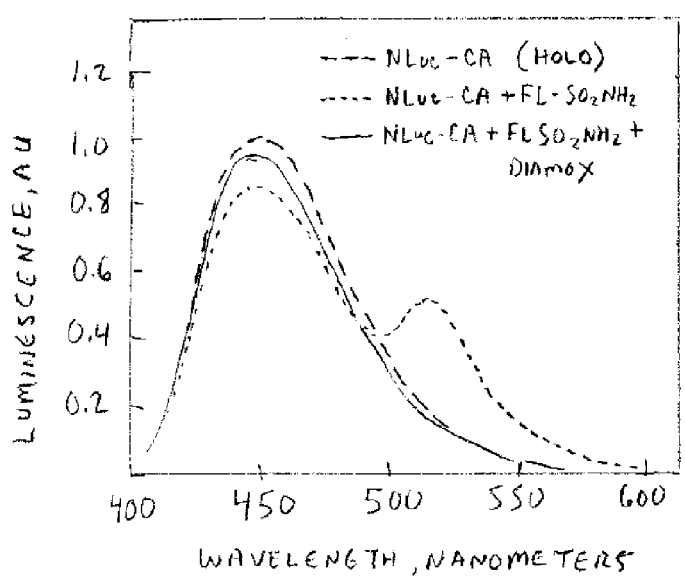
FIG. 4 shows bioluminescence emission spectra of apo-NanoLuc-CA(--curves), apoNanoLuc-CA in 19 nM free Zn plus fluorescein sulfonamide (••••••) and after addition of the competing nonfluorescent sulfonamide (-), showing that sulfonamide binding is specific.
Figure 5:
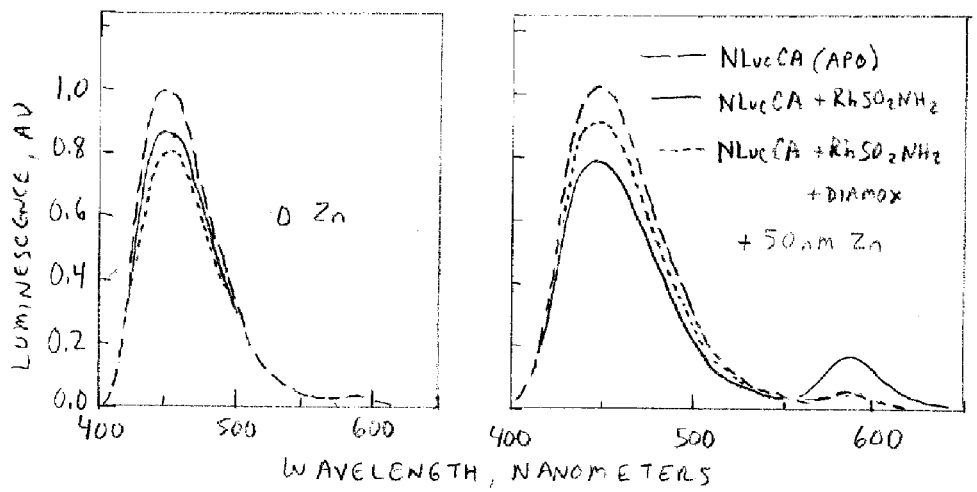
FIG. 5 shows bioluminescence emission spectra of NanoLuc-apoCA alone (curves), plus LISSAMINE rhodamine sulfonamide (-) and following addition of high affinity sulfonamide Diamox (••••••); the left panel is at femtomolar free zinc, and the right panel at 50 nanomolar free zinc.
Figure 6:
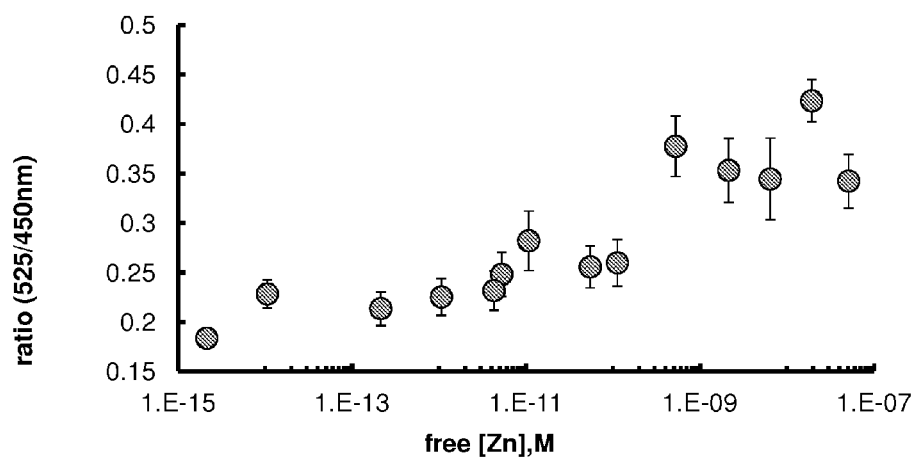
FIG. 6 shows zinc-dependent emission ratios of NanoLuc-apoCA plus fluorescein sulfonamide.
Figure 7:
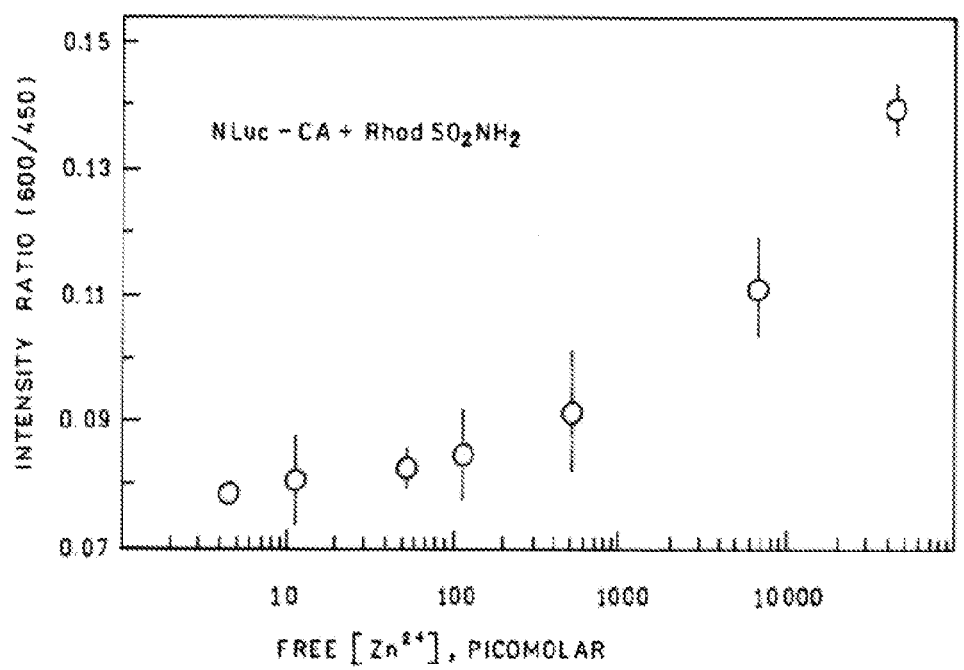
FIG. 7 shows zinc-dependent intensity ratios of NanoLuc-apoCA plus LISSAMINE rhodamine sulfonamide.

In another preferred embodiment the luciferase gene fused to the human carbonic anhydrase II gene is from a variant of the luciferase isolated from the deep sea shrimp *Oplophorus gracilirostris* (offered commercially by Promega as Nanoluc), and the luciferin is a coelenterazine derivative called furimazine ("Engineered Luciferase Reporter from a Deep Sea Shrimp Utilizing a Novel Imidazopyrazinone Substrate" by Mary P. Hall †, James Unch ‡, Brock F. Binkowski †, Michael P. Valley †, Braeden L. Butler †, Monika G. Wood †, Paul Otto †, Kristopher Zimmerman †, Gediminas Vidugiris †, Thomas Machleidt †, Matthew B. Robers †, Hélène A. Benink †, Christopher T. Eggers †, Michael R. Slater †, Poncho L. Meisenheimer ‡, Dieter H. Klaubert ‡, Frank Fan †, Lance P. Encell *†, and Keith V. Wood † *ACS Chem. Biol.,* 2012, 7 (11), pp 1848-1857DOI: 10.1021/cb3002478). In the absence of zinc and a suitable fluorescent sulfonamide (fluorescein sulfonamide or LISSAMINE rhodamine sulfonamide, see below), one only observes emission from the luciferase characteristically peaking at 460 nm; as zinc ion is added the sulfonamide binds and one also observes emission at wavelengths characteristic of the sulfonamide included: 510 nm for the fluorescein sulfonamide (FIGS. 4) and 590 nm for the RHODAMINE sulfonamide (FIG. 5) The Nanoluc-CA fusion protein thus exhibits zinc-dependent changes in the ratio of emission intensity from the luciferase to that of the sulfonamide in both cases (FIGS. 6 and 7). An important advantage of this ratiometric approach is that it is essentially independent of time-dependent changes in bioluminescence emission, which are frequently observed.

The invention is also embodied in the form of kits that can be used to prepare samples for determination of metal ions. Such a kit comprises one or more of the apoCA-luciferase conjugates or fusion proteins (optionally further conjugated with an intermediate acceptor fluorophore), the appropriate substrates for the luciferase portion of the conjugate or fusion protein(s) (e.g. furimazine or coelenterazine in the instance of the *Oplophorus* luciferase), one or more fluorescent sulfonamides suitable for FRET coupling with the luciferase (e.g. LISSAMINE rhodamine sulfonamide when *Oplophorus* luciferase is used), or suitable for FRET coupling to the intermediate acceptor fluorophore if that is present. The fluorescent sulfonamide(s) is(are) one(s) that binds the CA-luciferase conjugate or fusion protein when the metal ion binding site of the protein is occupied by a metal ion (preferably zinc or cadmium). Kits according to the invention may optionally further include an intermediate acceptor fluorophore and reagents for conjugating it to the CA conjugate or fusion protein, a competitor for the metal binding to the CA portion of the conjugate or fusion protein (e.g. Diamox) to assess specificity of the assay and (also optionally) a zinc buffer of known free zinc concentration (to provide calibration samples or positive control samples). Each of the reagents is packaged individually and then the individual packages are packaged together as a collection.

The present invention has among other advantages very great sensitivity. The method of the invention may in some embodiments successfully quantitate metal ion concentration down to $10^{-10}$ M, and in some instances as low as $10^{-12}$ M.

EXAMPLE 1

Assay using an *Oplophorus* luciferase

One uL of 1 nM Nanoluc-apoCA fusion protein dissolved in 10 mM HEPES buffer pH 7.5 is equilibrated with 140 uL of a pH 7.5 HEPES/nitrilotriacetic acid zinc buffer of specified free zinc ion concentration (for calibration), or an aqueous sample of the same volume and unknown free zinc concentration (for measurement), both containing 2 uM RHODAMINE sulfonamide at room temperature. The reaction is initiated by addition of furimazine (1 uL of 1 uM in DMF) or coelenterazine, and following brief agitation the emission spectrum is obtained from 400 to 700 nm in a suitable fluorometer without any exciting light.

EXAMPLE 2

Assay utilizing a Bacterial Luciferase

A further example employs a fusion protein of bacterial luciferase from *Vibrio harveyi*, with alpha and beta luciferase subunits fused with carbonic anhydrase with suitable intervening linkers, the whole expressed and purified by affinity chromatography using an aminomethylbenzene sulfonamide coupled to Sepharose resin (Sigma A-7096). The zinc is removed from the carbonic anhydrase (CA) to form apo-CA using dipicolinate dialysis as previously described (Pocker, Y., and Fong, C. T. O. (1983), Inactivation of bovine carbonic anhydrase by dipicolinate: Kinetic studies and mechanistic implications, *Biochemistry* 22, 813-818). The metal determination is performed in a manner similar to the luciferase activity assay well known to the art (J. W. Hastings, T. O. Baldwin, and M. Z. Nicoli, "Bacterial luciferase:Assay, purification, and properties," In *Methods in Enzymology Vol 57, Bioluminescence and Chemiluminescence*, pp. 135-152 (1978)) : luciferase apo-CA (1 nanomole) in 1 ml 10 mM MOPS pH 7.5 is gently mixed with 2 nanomoles LISSAMINE rhodamine sulfonamide, 20 microliters of myristaldehyde suspended in 0.1% Triton X-100 in water, and 1 ml aqueous sample with unknown free zinc concentration, then is placed in the sample chamber of a T-format fluorometer (Weber, G. (1956) Photoelectric method for the measurement of the polarization of the fluorescence of solutions, *Journal of the Optical Society of America* 46, 962-970.) such as an ISS Koala (Urbana, IL) with excitation turned off, with one emission filter with peak transmission at 490 nm in front of one detector, and a 600 nm peak transmission emission filter. Reduced flavin mononucleotide (FMNH$_2$) (1 ml of 50 uM in MOPS buffer) is forcefully injected into the cuvette and the ratio of intensities from the two detectors measured; the concentration is determined as above by comparison with intensity ratios of known free zinc concentrations. Other variations on this assay using continuous generation of the reduced FMNH$_2$ using NADH are also described in Hastings, et al.

Scheme 1: Synthesis of LISSAMINE rhodamine B sulfonamide (LISSAMINE rhodamine B sulfonamide ethyl phenyl sulfonamide) (upper panel) and fluorescein sulfonamide (fluorescein thioureidyl ethyl phenyl sulfonamide) (lower panel)

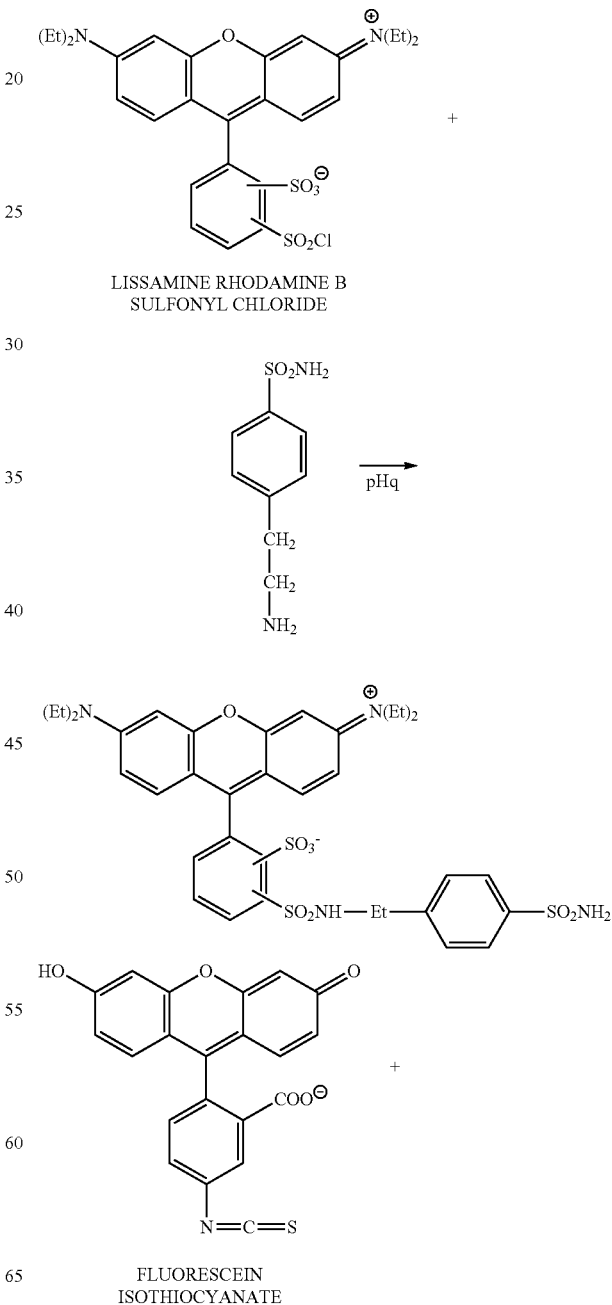

-continued

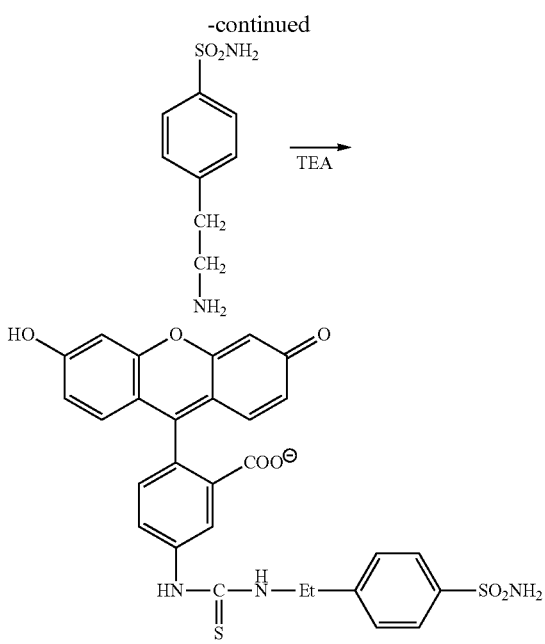

Synthesis of LISSAMINE rhodamine sulfonamido ethyl benzene sulfonamide (Scheme 1, upper): LISSAMINE rhodamine B sulfonyl chloride, 10 mg) is dissolved in 2 ml 100 mM triethylammonium bicarbonate buffer with 3.5 mg 4-(2'-aminoethyl)phenylsulfonamide in 1 ml DMF and stirred for 2 hours at room temperature. The reaction mixture is diluted in water, frozen, and lyophilized. The dried powder is dissolved in DMF and chromatographed on silica gel in ethyl acetate/methanol/(NH$_4$OH:H$_2$O 3:7) 15:3:3 and stripped of solvent by evaporation.

Synthesis of fluorescein thioureidyl ethyl phenyl sulfonamide (Scheme 1, lower) Fluorescein isothiocyanate (100 mg) is dissolved in 5 ml DMF, to which is added 200 mg 4-(2'-aminoethyl)phenylsulfonamide in 1 ml DMF including 130 ul triethylamine and stirred for 4 hours at room temperature, the reaction followed by TLC. The reaction mixture is diluted in water, frozen, and lyophilized. The dried powder is dissolved in DMF and chromatographed on silica gel in 3:1 ethyl acetate: hexanes and stripped of solvent by evaporation.

Additional References

Bozym, R., T. K. Hurst, et al. (2008). Determination of zinc using carbonic anhydrase-based fluorescence biosensors. *Fluorescence Spectroscopy*. L. Brand and M. Johnson. San Diego, Academic Press. 450: 287-309.

Bozym, R. A., R. B. Thompson, et al. (2006). "Measuring Picomolar Intracellular Exchangeable Zinc in PC-12 Cells Using a Ratiometric Fluorescence Biosensor." *ACS Chem. Biol.* 1(2): 103-111.

Elbaum, D., S. K. Nair, et al. (1996). "Structure-based design of a sulfonamide probe for fluorescence anisotropy detection of zinc with a carbonic anhydrase-based biosensor." *Journal of the American Chemical Society* 118(35): 8381-8387.

Forster, T. (1948). "Intermolecular energy migration and fluorescence (Ger.)." *Annalen der Physik* 2: 55-75.

McCranor, B., R. Bozym, et al. (2012). "Quantitative imaging of mitochondrial and cytosolic free zinc levels in an in vitro model of ischemia/reperfusion." *Journal of Bioenergetics and Biomembranes* 44(2): 253.

McCranor, B. J., R. A. Bozym, et al. (2012). "Quantitative imaging of mitochondrial and cytosolic free zinc levels in an in vitro model of ischemia/reperfusion." *Journal of bioenergetics and biomembranes* 44(2): 253-263.

Schwarze, S. R., A. Ho, et al. (1999). "In vivo protein transduction: Delivery of a biologically active protein into the mouse." *Science* 285: 1569-1572.

Stumm, W. and J. J. Morgan (1996). *Aquatic Chemistry: Chemical Equilibria and Rates in Natural Waters.* New York, Wiley-Interscience.

Thompson, R. B. (1991). Fluorescence-based fiber optic sensors. *Topics in Fluorescence Spectroscopy Vol. 2: Principles.* J. R. Lakowicz. New York, Plenum Press. 2: 345-365.

Thompson, R. B. (1994). "Fiber optic chemical sensors." *IEEE Proceedings on Circuits and Devices* CD-10(3): 14-21.

Thompson, R. B., M. L. Cramer, et al. (2002). "Excitation ratiometric fluorescent biosensor for zinc ion at picomolar levels." *Journal of Biomedical Optics* 7(4): 555-560.

Thompson, R. B., Z. Ge, et al. (1996). *Determination of multiple analytes using a fiber optic biosensor based on fluorescence energy transfer.* Ultrasensitive Biochemical Diagnostics, San Jose, Calif., Society of Photooptical Instrumentation Engineers.

Thompson, R. B., Z. Ge, et al. (1996). "Fiber optic biosensor for Co(II) and Cu(II) based on fluorescence energy transfer with an enzyme transducer." *Biosensors and Bioelectronics* 11(6): 557-564.

Thompson, R. B., Hui-Hui Zeng, et al. (2008). Instrumentation for fluorescence-based fiber optic biosensors. *Fluorescence Spectroscopy*. L. Brand and M. L. Johnson. San Diego, Academic Press. 450: 311-337.

Thompson, R. B., W. O. W. Jr., et al. (2000). "Fluorescence microscopy of stimulated Zn(II) release from organotypic cultures of mammalian hippocampus using a carbonic anhydrase-based biosensor system." *Journal of Neuroscience Methods* 96(1): 35-45.

Thompson, R. B., B. P. Maliwal, et al. (1998). "Expanded dynamic range of free zinc ion determination by fluorescence anisotropy." *Analytical Chemistry* 70(9): 1749-1754.

Thompson, R. B., B. P. Maliwal, et al. (2000). "Zinc biosensing with multiphoton excitation using carbonic anhydrase and improved fluorophores." *Journal of Biomedical Optics* 5(1): 17-22.

Thompson, R. B. and M. W. Patchan (1995). "Fluorescence lifetime-based biosensing of zinc: origin of the broad dynamic range." *Journal of Fluorescence* 5: 123-130.

Thompson, R. B., H. H. Zeng, et al. (2000). *Issues in enzyme-based metal ion biosensing in complex media.* In-vitro Diagnostic Instrumentation, San Jose, Calif., SPIE.

Wang, D., T. K. Hurst, et al. (2011). "Genetically encoded ratiometric biosensors to measure extracellular exchangeable zinc in *Escherichia coli*." *Journal of Biomedical Optics* 16(8): 087011-087011-087011-087011.

Zeng, H. H., R. B. Thompson, et al. (2003). "Real-time determination of picomolar free Cu(II) in seawater using a fluorescence-based fiber optic biosensor." *Analytical Chemistry* 75(24): 6807-6812.

We claim:

1. A method for determining metal ions comprising contacting a sample, a cell, or a tissue with a luciferase-conjugated apocarbonic anhydrase; contacting the sample, cell or tissue with an ultimate acceptor ligand; adding one or more luciferase substrates; measuring light emitted from the sample, cell or tissue; thereby determining the metal ions in the sample, cell or tissue.

2. The method of claim 1, wherein the metal ion is Zn(II) or Cd(II).

3. The method of claim 1, wherein the luciferase is one from a *Photinus* (firefly) species, a *Renilla* (dinoflagellate) species or an *Oplophorus* (deep sea shrimp) species.

4. The method of claim 1, in which metal ions are determined in a sample that is a bodily fluid.

5. The method of claim 3, wherein the substrates are the luciferin from the same species as the luciferase conjugated to the carbonic anhydrase, and adenosine trisphosphate.

6. The method of claim 1, in which metal ions are determined in a sample that is sea water, fresh water, drinking water, or waste water, ground water, or process water.

7. The method of claim 1, wherein the ultimate acceptor ligand binds to the luciferase-conjugated carbonic anhydrase if and only if the metal ion is present in the carbonic anhydrase active site.

8. The method of claim 1, wherein the ultimate acceptor ligand is a fluorescent aryl sulfonamide.

9. The method of claim 8, wherein the ultimate acceptor ligand is LISSAMINE rhodamine sulfonamide or fluorescein sulfonamide.

10. The method of claim 1, wherein the emission is at the characteristic wavelengths of the ultimate acceptor ligand.

11. The method of claim 1, wherein the concentration of the metal ion is proportional to the ratio of the emission at a characteristic wavelength of the ultimate acceptor ligand to the emission at a characteristic wavelength of the luciferase.

12. The method of claim 1, wherein the luciferase is conjugated to the carbonic anhydrase by fusing their genes together in a single piece of DNA and expressing the fusion protein.

13. The method of claim 1, wherein the luciferase protein is conjugated by covalently attaching the luciferase protein to carbonic anhydrase.

14. The method of claim 1, wherein the carbonic anhydrase is human carbonic anhydrase isozyme II.

15. The method of claim 14, wherein the carbonic anhydrase is wild type human carbonic anhydrase, or a Q92A, E117A, H94N, H36C, or C206S variant thereof.

16. The method of claim 13, wherein the luciferase is conjugated to the carbonic anhydrase using a heterobifunctional crosslinker.

17. The method of claim 16, wherein the heterobifunctional crosslinker is sulfo-SMCC and the carbonic anhydrase is an H36C variant of human carbonic anhydrase.

18. The method of claim 1, wherein the luciferase is biotinylated and the carbonic anhydrase is conjugated to steptavidin.

19. The method of claim 1, wherein an intervening acceptor is conjugated to the luciferase-carbonic anhydrase conjugate.

20. The method of claim 1, wherein the luciferase is a bacterial luciferase.

21. A method for determining metal ions comprising contacting a sample, a cell, or a tissue with a luciferase-conjugated apocarbonic anhydrase; contacting the sample, cell or tissue with an ultimate acceptor ligand; adding one or more luciferase substrates; measuring light emitted from the sample, cell or tissue; and correlating the amount of emitted light to the concentration of the metal ions in the sample, cell or tissue or correlating the ratio of light emitted from the sample, cell or tissue at two different wavelengths with the concentration of the metal ions in the sample, cell or tissue, thereby determining the concentration of metal ions in the sample, cell or tissue.

22. The method of claim 21, in which the concentration of free metal ions is determined.

23. The method of claim 21, wherein the metal ion is Zn(II) or Cd(II).

24. The method of claim 22, wherein the metal ion is Zn(II) or Cd(II).

25. The method of claim 21, in which the metal ion concentration can be determined to a concentration of $10^{-10}$ molar.

26. The method of claim 1, wherein the luciferase is non-covalently associated with the carbonic anhydrase.

* * * * *